United States Patent [19]

Takahashi et al.

[11] 4,334,433
[45] Jun. 15, 1982

[54] METHOD AND APPARATUS FOR MEASURING THICKNESS OF CLAD STEEL

[75] Inventors: Shizuo Takahashi; Satoru Matsumi; Toshiyuki Sugiyama; Susumu Takeda, all of Muroran, Japan

[73] Assignee: Japan Steel Works, Ltd., Tokyo, Japan

[21] Appl. No.: 152,053

[22] Filed: May 20, 1980

[30] Foreign Application Priority Data

Nov. 25, 1978 [JP] Japan .................................. 53-145520

[51] Int. Cl.³ ............................................ G01N 29/00
[52] U.S. Cl. .................................................... 73/629
[58] Field of Search ................. 73/629, 627, 597, 598; 367/99

[56] References Cited

U.S. PATENT DOCUMENTS 3,643,494  2/1972  Kammer ................................ 73/629
3,918,296  11/1975  Kitada ................................... 73/627
3,985,022  10/1976  Dileo ..................................... 73/629

FOREIGN PATENT DOCUMENTS 838922  6/1960  United Kingdom ................. 73/629

OTHER PUBLICATIONS

Krautkramer, *Ultrasonic Testing of Materials*, Sect. 14.5, pp. 318-324, 1977.
Krautkramer, *Ultrasonic Testing of Materials*, Sect. 10.2.2, pp. 202-205, 1977.

Primary Examiner—Anthony V. Ciarlante
Attorney, Agent, or Firm—Sughrue, Mion, Zinn, Macpeak and Seas

[57] ABSTRACT

A method and apparatus for measuring the thicknesses of a cladding layer and a base metal layer by applying ultrasonic waves on the side of a sample opposite the cladding layer. The reflected waves are sensed and displayed on an oscilloscope. Using a disclosed technique for eliminating noise and interference, the position of the interface between the cladding layer and base metal layer are measured from a pulse produced due to the discontinuity of acoustic impedance at the interface.

4 Claims, 10 Drawing Figures

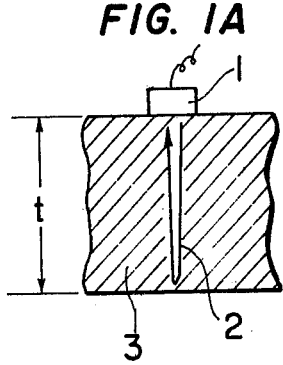
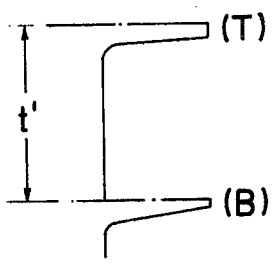
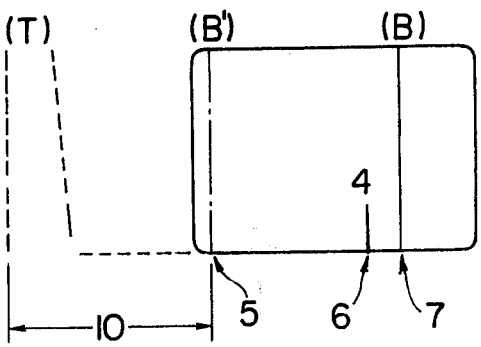

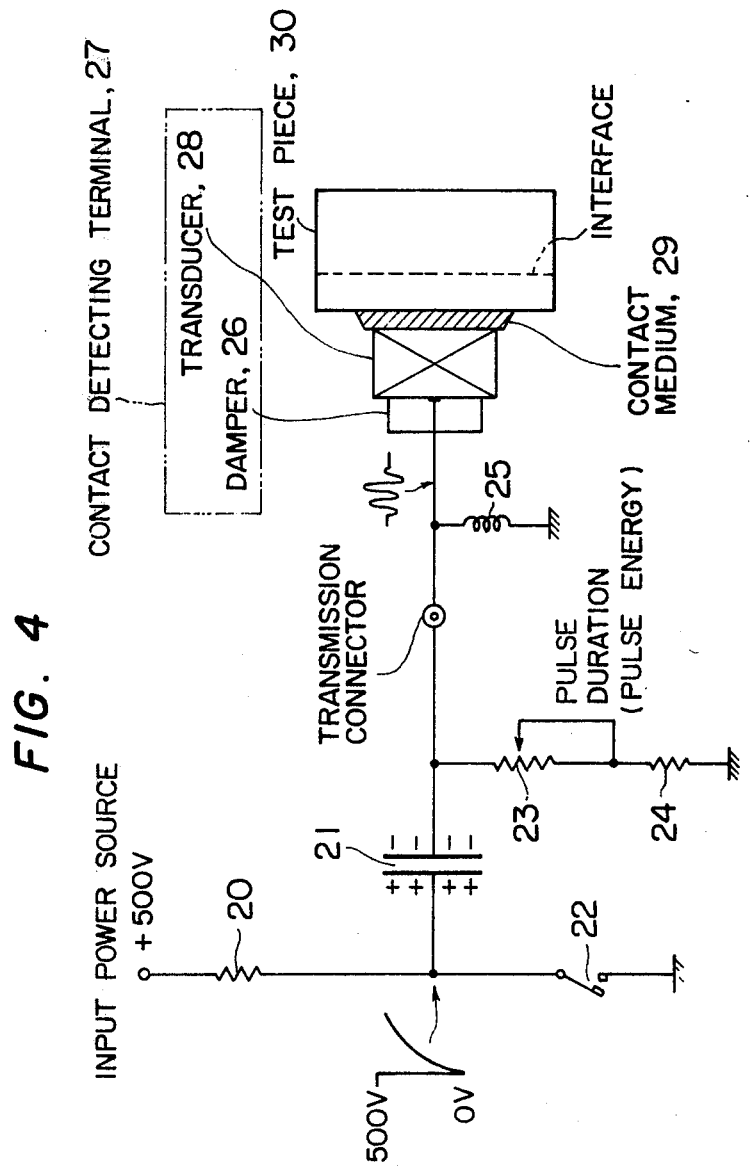

METHOD AND APPARATUS FOR MEASURING THICKNESS OF CLAD STEEL

BACKGROUND OF THE INVENTION

The present invention relates to a method for precisely and positively measuring the separate thicknesses of a base metal and a clad metal layer thereon, the total thickness thereof with an electromagnetic crack test, and an apparatus for implementing the method.

So-called clad steel is broadly used in various industrial fields because it is very economical and also durable. Clad steel is so formed with a material such as stainless steel, titanium, aluminum, copper or an alloy thereof, which is different from the base metal, metallurgically overlaid on one side or both sides of the base metal such as carbon steel or low alloy steel by hot rolling, explosive adhesion or welding.

Such clad steel is particularly well adapted for use in a corrosive environment. However, in such applications, it is particularly important to maintain a proper thickness of the cladding material which forms the corrosion resistant layer.

Various methods for measuring the thickness of the cladding material or layer have been proposed. In a first such method, the thickness of the layer is mechanically measured with a measurement tool after etching away a peripheral portion. In a second prior art method, the overall thickness including that of the base metal is measured using a supersonic thickness gauge and the thickness of the cladding layer is calculated. In a third method, the thickness of the cladding layer is measured using an electromagnetic minute thickness detector to measure the variation of magnetic permeability caused by the cladding layer.

The above described conventional methods have the following drawbacks. The first mechanical method is only applicable for measuring a marginal portion of the clad steel. With this method, it is impossible to measure the thickness over the entire clad steel surface particularly at locally changed portions which may be formed due to forming compression. The second method in which a supersonic thickness gauge is employed may be used for measuring the thickness over the entire clad steel surface but it is impossible to use it to measure changes of the thickness due to variations in the forming rates of the cladding layer and the base metal. The third method wherein a electromagnetic minute thickness detector is used is applicable only to measurement of the cladding layer and its measuring precision is very low. In addition, the method is not applicable to the measurement of a cladding layer having magnetic properties.

SUMMARY OF THE INVENTION

It is thus a primary object of the invention to provide a measuring technique which is essentially free of each of the aforementioned drawbacks.

According to the invention there is provided a method which takes into account the differences in acoustic impedances of the base material and the cladding material thereon. A metallic compound at the interface between the cladding material and the base material forms having crystals of different crystal grain. Because of the difference in crystal grain arrangement at the interface, upon applying ultrasonic waves, an echo is generated at the interface due to the difference in structure of the two chemical compounds. The echo is amplified and rectified and from the resulting signal the thickness of the cladding material can be precisely and positively measured over the entire surface of the material. Such a measurement has hitherto been considered impossible.

According to the present invention, it is possible to measure the thickness of clad steel which may in fact vary during manufacture or may change due to aging so that such clad material, once it passes such inspection, may be used with complete confidence and safety.

BRIEF DESCRIPTION OF THE DRAWINGS

FIGS. 1A and 1B are diagrams for illustrating the principle of measurement of using supersonic waves employed with the invention;

FIGS. 2A to 2D show successive states of measuring the clad steel according to the method of the present invention;

FIGS. 3A and 3B show another method according to the present invention;

FIG. 4 is a schematic diagram of an input circuit used with the invention; and

DESCRIPTION OF THE PREFERRED EMBODIMENTS

Figure 5:
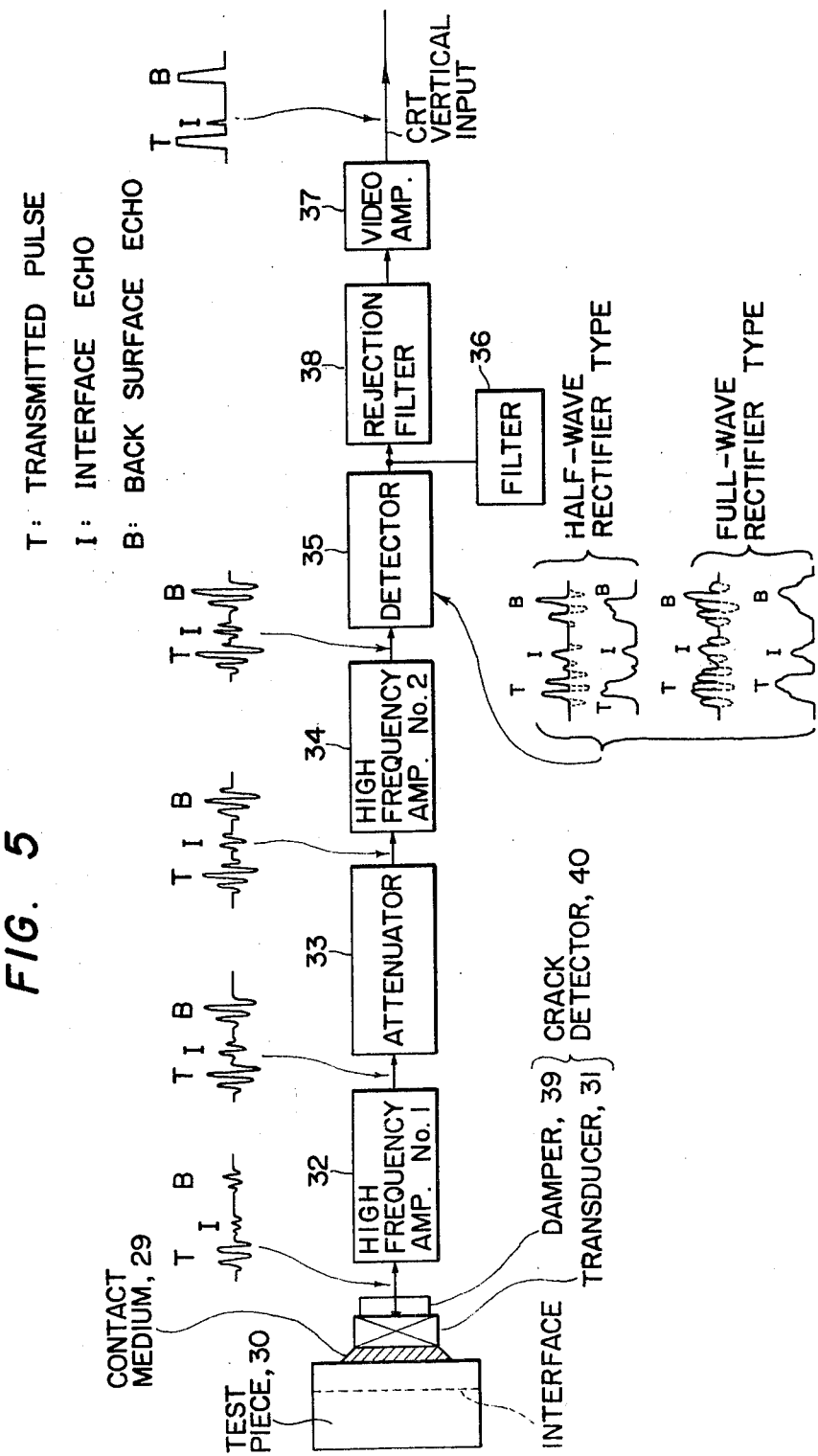
FIG. 5 is a block schematic diagram of an output circuit used with the invention.

The present invention will be hereinafter described with reference to the accompanying drawings.

FIGS. 1A and 1B illustrate the principle of measurement of thickness of a test piece using supersonic waves according to the invention. With the assumption that the speed of sound is constant in a uniform material, a supersonic wave 2 is emitted from a contact detecting terminal 1 travelling through the material being reflected back to the transducer 1 from the lower surface of the material. FIG. 1B shows an image on cathode-ray tube oscilloscope corresponding to FIG. 1A. The position of a bottom surface echo B is indicated on the oscilloscope tube in which the total thickness t or the material is proportional to a length t'.

The relationship between the scale of the time axis and the actual thickness measured may be calibrated by using a test piece having a known thickness in which the speed of sound is constant from which the thickness t is measured by reading out on the time axis the position of the bottom surface echo B of the test material being measured.

Supersonic waves have the property that when they pass through materials different in acoustic impedance, a part or most of the supersonic waves is reflected at the interface therebetween. The greater the difference in the acoustic impedance, the greater is the amount of such reflection.

Reflections often occur due to differences in the size of the crystal grain or its arrangement or they may occur because of differences in chemical composition. Taking advantage of the above-noted property of supersonic waves, the present invention provides a method and an apparatus utilizing this supersonic wave property to thereby measure the thicknesses of the cladding layer and the base metal of the clad steel.

An embodiment for measuring the respective thickness of the cladding layer and the base metal will be described in which the base metal is made of carbon steel having a small difference in its acoustic impedance from that of a cladding layer thereon which is made of stainless steel with accordingly only a very weak echo generated at the interface therebetween. It should be noted that in case of other cladding materials such as aluminum, copper and alloys thereof, the differences of their acoustic impedances from that of the base metal are much greater than in this example. That is, it is easier to measure the thicknesses.

The method of the present invention differs significantly from those described before. According to the present invention, a weak interface echo is clearly separated just in front of the bottom surface echo with a precision of at least 10 times that previously obtainable by amplifying the gain, enhancing the pulse output, and displaying the shape of the echo signal on an oscilloscope tube. Therefore, it is possible to precisely read out the thicknesses of the base material and the cladding material.

With the present invention, a wide-band high damping contact detecting terminal having a wide frequency spectrum and a damping constant so as to make the signals highly resolvable and a supersonic crack detector are employed. The supersonic crack detector has the following properties.

(1) An echo having a narrow width is faithfully amplified by means of a wide-band amplifying circuitry having a bandwidth above 0.5 MHz and in which the gain is constant over a wide frequency range.

(2) In regard to the oscilloscope employed, the gain for input signals should be continuously variable.

(3) Also, the time axis position on the oscilloscope should be capable of moving an image point beyond a scale length corresponding to the thickness of the material to be measured. For example, for an oscilloscope in which the measurable range is limited to 10.0 mm, the minimal scale units of the time axis should correspond at least to 0.2 mm.

(4) Amplifying rectilinear propagation is not affected by the rejection with respect to an echo producing a signal amplitude higher than the maximum scale of the oscilloscope. The adjustment of the rejection is continuously variable.

(5) The time axis scale on the oscilloscope is divided into at least fifty equidistant scale units.

(6) A measurement range of 10 mm or less can be sufficiently enlarged.

FIGS. 2A to 2D show oscilloscope displays for the embodiment in which by using thus constructed contact detecting terminal and supersonic crack detector, the clad steel plate is measured from the base material surface side. The base material and the cladding material for this example are AST 7A 440 and AISI 304, respectively, and have thicknesses of 7.8 mm and 2.0 mm, respectively. The total thickness thereof is thus 9.8 mm.

FIG. 2A shows a state in which the pulse width from the interface echo and the rejection of the crack detector are maintained at zero levels and the gain is set to $B_1 = 100\% + 26$ dB so that an initial echo 4 can just be seen. In FIG. 2A, T designates the transmitted pulse and B a bottom echo from the outside face of the sample. When the interface echo is seen, the pulse width thereof is increased by changing the time axis scale while the time delay of the oscilloscope is adjusted to maintain the position of the pulse constant on the display screen. Thus, while the state shown in FIG. 2B is maintained, effectively only the rejection is increased to eliminate the noise echo. The resulting interface echo 4 can be clearly seen in the form of a line in FIG. 2C. As described above, by matching gain, pulse width and rejection, an interface echo having a sharp initial rise can be displayed on the display screen of the oscilloscope.

The time axis is in advance determined by accurate calibration using a known test piece. The measurable range is established in order to include the total thickness of the material to be measured. Since a surface 5 of the material which the contact detecting terminal contacts is coincident with at the zero point, the distance from this surface to the position 6 of the rise of the interface echo 4 represents the thickness of the base material and the distance from the rising position 6 of the interface echo 4 to the rising position 7 of the bottom surface echo B represents the thickness of the cladding layer 10. Also, the distance from the surface 5 to the position 7 of the bottom echo B represents the total thickness. To obtain thickness measurements, the distance between these positions are scaled in accordance with the velocity of sound of the various materials.

FIG. 3 shows a case where a thickness of 10 to 20 mm is measured in substantially the same manner as in the previous example. In this case, if the above-described rising position of the bottom surface echo B' which has been already calibrated is moved to the zero point 5 by using the time axis adjustment feature of the oscilloscope, the real measurable range is 10 to 20 mm. The thickness can be obtained by adding 10 mm to the direct scale readout at the position 6 to 7 corresponding to the interface echo or the bottom surface echo. In the same manner, a much greater thickness or depth can be measured in order to maintain the range of measurement within 10 mm at all times. Therefore, a high accurate measurement can uniformly be achieved.

As described above, according to the present invention, it is possible to measure the thickness of the cladding material layer of clad steel which has hitherto been considered impossible. According to the invention, it is possible to very precisely measure the thickness at any position of the clad steel within ±1 mm with ease and also to measure the thickness from either surface side or backside.

If the total thickness of the clad steel is more than 2.5 mm and that of the cladding material is more than 0.4 mm, it is quite easy to measure both thicknesses. It is also possible to measure a thickness of a material having a curvature of more than 1.5 times that of the contact detecting terminal diameter which has a cylindrical or arcuate shape.

Therefore, according to the present invention, the thickness of the cladding layer processed through forming can be precisely known. This is economical because the use of expensive material can be minimized.

Referring next to FIG. 4 there is shown therein a schematic diagram of the contact detecting terminal and associated circuitry used for generating ultrasonic pulses. A resistor 20 is connected between a source of DC voltage, for example 500 volts, and one terminal of a switch 22, the other terminal of which is connected to ground. Switch 22 is preferably a silicon controlled rectifier or other semiconductor switch. Switch 22 is operated periodically at a convenient rate for the oscilloscope. One terminal of a capacitor 21 is connected to the junction between resistor 20 and switch 22 while the other terminal is coupled through a series combination of variable resistor 23 and fixed resistor 24 to ground. Adjustment of variable resistor 23 determines the pulse width or pulse energy of pulses through capacitor 21. The junction of capacitor 21 and variable resistor 23 is coupled to coil 25, the other terminal of which is coupled to ground. The common point of capacitor 21, variable resistor 23 and coil 25 are connected to the input terminal of wide-band transducer 28 of contact detecting terminal 27. Contact detecting terminal 27 also includes a piece of damper material 26 disposed upon the backside of transducer 28 to prevent ringing thereof. Contact detecting terminal 27 may, for example, be a model CLF-5 contact detecting terminal manufactured by Krautkraemer Company of West Germany. Preferably, transducer 28 is ultrasonically coupled to test piece 30 by the use of a contact medium 29 such as a gel or the like, a number of types of which are commercially available.

Referring next to FIG. 5, there is shown therein a block schematic diagram of the supersonic crack detector and associated circuitry utilized with the invention. A transducer 31 of the crack detector 40 is ultrasonically coupled to test piece 30 by the use of contact medium 29. Preferably, transducer 31 of crack detector 40 and transducer 28 of contact detecting terminal 27 are physically located adjacent one another in a probe. Also similar to the case of contact detecting terminal 27, a piece of damper material 39 is disposed at the rear of transducer 31 of crack detector 40. The output of transducer 31 is fed through a high frequency amplifier 32, attenuator 33 and second high frequency amplifier 34 to the input of detector 35. The waveforms at various points along this circuit are indicated on the diagram of FIG. 5. Detector 35 may be constituted by either a half-wave rectifier or full-wave rectifier as desired. The output waveforms from detector 35 are indicated for both types of rectifiers. Filters 36 and 38 are coupled to the output of detector 35. Filter 38 is a rejection filter which reduces the high frequency components in the output of detector 35. Preferably, rejection filter 38 is adjustable so that the operator can obtain the clearest possible output waveform. The output of rejection filter 38 is coupled through a wide-band video amplifier 37 to the vertical input terminal of the cathode-ray tube oscilloscope with which the circuit is used. Crack detector 40 may, for example, be constituted by a model USL-32 crack detector manufactured by Krautkraemer Company of West Germany.

What is claimed:

1. A method for measuring the thickness of various layers of a multilayered metal member having at least a first surface, a second surface and an interface surface between said first and second surface comprising the steps of:

providing contact detecting terminal means having wideband and high damping means and supersonic wave crack detector means having wide-band amplifying means at a position adjacent said first surface of said metal member;

coupling said crack detector to an oscilloscope having a continuously adjustable time scale;

displaying pulses representative of said first and second surfaces on said oscilloscope by operation of said contact detecting terminal means and said supersonic wave crack detector means;

maintaining a displaying pulse representative of said first surface at a zero level by appropriate rejection of signals produced by said crack detector and increasing the gain thereof so that an interface echo can be seen between said displayed signals representative of said first surface and said second surface;

adjusting the time axis scale of said oscilloscope to increase the pulse width of said interface echo so that said interface echo increases in amplitude; and increasing said rejection of signals produced by said crack detector to thereby delete noise echos generated from said increase in the pulse width of said interface echo to cause said interface echo to be displayed as a clear wave shape whereby said clear wave shape is representative of said interface surface between said first and second surfaces.

2. An apparatus for measuring thicknesses of various layers of a multilayered metal member comprising:

wide-band and high-damping contact detecting terminal means having a wide bandwidth and a high damping effect;

supersonic wave crack detecting means;

wide-band amplifier means for amplifying signals produced by said crack detecting means and rejection filter means coupled to said amplifying means; and a cathode-ray tube oscilloscope having an input connected to said crack detecting means.

3. The thickness measuring apparatus of claim 2 further comprising pulse generating means coupled to said contact detecting terminal means, said pulse generating means comprising a first resistor and a periodically-operated electronic switch coupled between terminals of a DC voltage source, a capacitor having a first terminal coupled to a junction between said first resistor and said switch, a variable resistor and second resistor coupled in series with one another and coupled between a second terminal of said capacitor and a ground terminal of said DC voltage source and an inductor having a first terminal coupled to said second terminal of said capacitor and a second terminal coupled to said ground terminal, said first terminal of said inductor being coupled to an input terminal of said contact detecting terminal means.

4. The thickness measuring apparatus of claim 2 or 3 further comprising detector means coupled to an output of said wide-band amplifier means, said rejection filter means being coupled to an output of said detector means.

* * * * *